United States Patent [19]

Greenleaf et al.

[11] Patent Number: 5,565,327
[45] Date of Patent: Oct. 15, 1996

[54] METHODS OF DIAGNOSING PARASITIC INFECTIONS AND OF TESTING DRUG SUSCEPTIBILITY OF PARASITES

[75] Inventors: Arno L. Greenleaf; Jae M. Lee, both of Durham, N.C.; Steven E. Hardin, Louisville, Ky.

[73] Assignee: Duke University, Durham, N.C.

[21] Appl. No.: 218,027

[22] Filed: Mar. 25, 1994

[51] Int. Cl.$^6$ ............................... C12Q 1/42; C12Q 1/04
[52] U.S. Cl. ................................. 435/21; 435/24; 435/34; 436/811
[58] Field of Search ................................. 435/21, 24, 32, 435/34, 194; 436/63, 811

[56] References Cited

U.S. PATENT DOCUMENTS

| | | | |
|---|---|---|---|
| 5,061,788 | 10/1991 | Certa | 530/350 |
| 5,112,749 | 5/1992 | Brey | 435/172.3 |

OTHER PUBLICATIONS

Knighton et al., Structure of a Peptide Inhibitor Bound to the Catalytic Subunit of Cyclic Adenosine Monophosphate–Dependent Protein Kinase, *Science*, 253:414–420 (1991).

Lee et al., CTD kinase large subunit is encoded by CTKI, a gene required for normal growth of Saccharomyces cerevisiae, *Gene Expression*, 1:149–167 (1991).

Giesecke et al., The C-Terminal Domain of RNA Polymerase II of the Malaria Parasi, *Biochemical and Biophysical Research Communications*, 180:1350–1355 (1991).

Li et al., An enlarged largest subunit of Plasmodium falciparum RNA polymerase II defines conserved and variable RNA polymerase domains, *Nucleic Acids Research*, 17:9621–9636 (1989).

Allison et al., The C–Terminal Domain of the Largest Subunit of RNA Polymerase II of Saccharomyces cerevisiae, Drosophila melanogaster, and Mammals: a Conserved Structure with an Essential Function, *Molecular and Cellular Biology*, 8:321–329 (1988).

Weeks et al., Locus–specific variation in phosphorylation state of RNA polymerase II in vivo: correlations with gene activity and transcript process, *Genes & Development*, 7:2329–2344 (1993).

Lee et al., A protein kinase phosphorylates the C–terminal repeat domain of the largest subunit of RNA polymerase II, *Biochemistry*, 86:3624–3628 (1989).

Drug Resistance in Malaria, *WHO Technical Report Series*, No. 529, pp. 102–118 (1973).

Lee, JM., CTD Kinase Large Subunit is Encoded . . . Gene Expression vol. 1 #2, May 1991 pp. 149–167.

Giesecre H., The C–Terminal Domain of RNA . . . Biochem Biophys Res Com vol. 180 #3, 1991 pp. 1350–1355.

*Primary Examiner*—Ralph J. Gitomer
*Attorney, Agent, or Firm*—Bell, Seltzer, Park & Gibson

[57] ABSTRACT

The CTD kinase of sporozoan parasites displays a specificity distinct from the analogous activity in mammalian cells. Methods of diagnosing blood borne Plasmodium parasites, and of testing the susceptibility of Plasmodium parasites to anti-malarial drugs, are based on this specificity.

5 Claims, 3 Drawing Sheets

METHODS OF DIAGNOSING PARASITIC INFECTIONS AND OF TESTING DRUG SUSCEPTIBILITY OF PARASITES

This invention was made with government support under Grant No. GM 40505 awarded by the National Institutes of Health. The government has certain rights in the invention.

FIELD OF THE INVENTION

The present invention relates to a protein kinase that hyperphosphorylates RNA polymerase II general, and particularly relates to this enzyme in parasites. The present invention further relates to substrate analogs and inhibitors of this enzyme and to methods of diagnosing and treating parasite-caused diseases using such analogs and inhibitors.

BACKGROUND OF THE INVENTION

In a large variety of eukaryotic species the largest subunit of nuclear RNA polymerase II (RPII) contains a region known as the C-terminal domain ("CTD"). The CTD of human beings and other mammals such as mice consists of 52 repeats of the consensus heptamer Tyr-Ser-Pro-Thr-Ser-Pro-Ser, while the CTDs of most lower eukaryotes consist of fewer repeats of the same consensus sequence. The CTD of the yeast *Saccharomyces cerevisiae*, for example, contains 26 repeats of this heptamer, the CTD of the fruit fly Drosophila contains 45 repeats, and the malarial parasite *Plasmodium falciparum* contains 17 repeats. The repeating heptamers may not match the consensus sequence exactly, for example, in *Saccharomyces cerevisiae* 17 of the 26 repeats exactly match the consensus heptamer Tyr-Ser-Pro-Thr-Ser-Pro-Ser, while in the CTD of Drosophila, only two of the 45 repeats are exact matches. A CTD region is not found in the homologous subunits of RNA polymerases I or III, or in the prokaryotic β' subunit.

While the repetitive CTD domain is conserved among a wide range of eukaryotic organisms, some eukaryotic RNA polymerase II contains a carboxy-terminus extension (CTE) rather than a CTD region. For example, the largest subunit of *Trypanosoma brucei* RNA polymerase II has a carboxy-terminus extension (CTE) consisting of 228 amino acids which is rich in serine and proline.

The CTD is essential for viability, as yeast or mouse cells containing RNA polymerase II from which all or most of the repeats have been removed do not grow. A notable feature of the CTD is that it is subject to hyperphosphorylation. A consequence of hyperphosphorylation is that the mobility in SDS gels of the largest RNA polymerase II subunit is markedly reduced. The mobility-shifted, hyperphosphorylated largest subunit is referred to as IIo, whereas the unphosphorylated subunit is referred to as IIa.

SUMMARY OF THE INVENTION

A first object of the present invention is a method for combatting a sporozoan infection in a mammalian subject by administering a sporozoan CTD kinase inhibitory binding ligand in an amount effective to decrease the number of parasites present in the subject over that which would occur without such treatment.

A further object of the present invention is a method of detecting sporozoan parasites in a mammalian subject. A biological sample is collected from the subject and contacted with (a) a sporozoan CTD kinase substrate equivalent and (b) a phosphate donor; and any hyperphosphorylation of the substrate equivalent is detected. Hyperphosphorylation indicates the presence of parasites in the sample.

A further object of the present invention is a method of testing the susceptibility of Plasmodium parasites to an anti-malarial drug. A test blood sample and a control blood sample are collected from a mammalian subject infected with the Plasmodium parasite; the anti-malarial drug in question is added to the test sample in an amount effective to eradicate susceptible Plasmodium parasites; and a sporozoan CTD kinase substrate equivalent and a phosphate donor are added to the samples. Reduced hyperphosphorylation in the test blood sample compared to the control blood sample indicates susceptibility of the parasite to the anti-malarial drug tested.

A further aspect of the present invention is a method for determining whether a host-parasite combination is amenable to anti-parasite treatment using CTD kinase inhibitors. The CTD region on the RNA polymerase II of the parasite is identified, as is the CTD region on the RNA polymerase II of the host. A parasite CTD kinase that specifically phosphorylates said parasite CTD region is identified, as is a host CTD kinase that specifically phosphorylates the host CTD region. The specificity of the kinases is compared to determine whether it is distinct from that of the host. If the parasite CTD kinase is distinct from the host CTD kinase, the host-parasite pair is suitable to anti-parasite treatment using CTD kinase inhibitors directed to the parasite CTD kinase which will inhibit the parasite CTD kinase but will not appreciably inhibit the host CTD kinase.

A further aspect of the present invention is a method for screening for anti-parasite compounds effective for anti-parasite therapy in a given parasite-host combination, where the parasite CTD kinase has a specificity distinct from that of the host. The parasite CTD kinase that specifically phosphorylates the parasite CTD region is identified. A combinatorial library is then screened for inhibitor molecules of the parasite CTD kinase, which do not inhibit host CTD kinase.

A further aspect of the present invention is a method of diagnosing a Plasmodium infection in a mammalian subject. A sample of blood is obtained from a mammalian subject and treated to lyse red blood cells and any Plasmodium cells present. Kinases are separated from the lysed sample and assayed with a known substrate of Plasmodium CTD kinase to determine whether the kinases phosphorylate the substrate. Phosphorylation of the substrate indicates the presence of Plasmodium organisms in the blood sample.

A further aspect of the present invention is a peptide having an amino acid sequence (Tyr-Ser-Pro-Thr-Ser-Pro-Lys)$_n$, (Tyr-Ala-Pro-Thr-Ala-Pro-Lys)$_n$, (Tyr-Ser-Pro-Thr-Ser-Pro-Arg)$_n$, or (Tyr-Ser-Pro-Thr-Ala-Pro-Arg)$_n$; where n is from one to one hundred, and where the peptide is capable of inhibiting sporozoan CTD kinase and incapable of inhibiting mammalian CTD kinase.

A further aspect of the present invention is a fusion protein comprising a peptide having amino acid sequence (Tyr-Ser-Pro-Thr-Ser-pro-Lys)$_n$, (Tyr-Ala-Pro-Thr-Ala-Pro-Lys)$_n$, (Tyr-Ser-Pro-Thr-Ser-Pro-Arg)$_n$, or (Tyr-Ser-Pro-Thr-Ala-Pro-Arg)$_n$; where n is from one to one hundred.

The foregoing and other objects and aspects of the present invention are explained in detail in the specification set forth below.

DETAILED DESCRIPTION OF THE INVENTION

Figure 2:
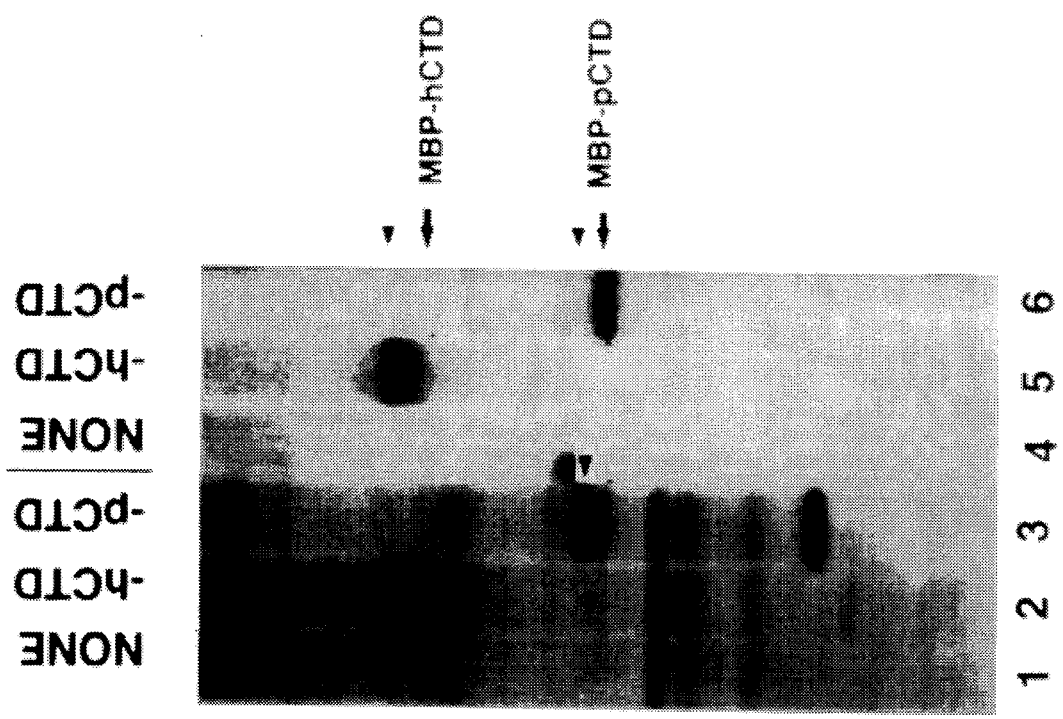
FIG. 2 is an autoradiogram comparing phosphorylation of the fusion proteins MBP-hCTD and MBP-pCTD by Plasmodium extract (from infected human cells) and HeLa cell extract.

Amino acid sequences disclosed herein are presented in the amino to carboxy direction, from left to right. The amino and carboxy groups are not presented in the sequence. Amino acid residues are represented herein by three letter code, in accordance with 37 CFR Section 1,822 and established usage. See, e.g., Patent In User Manual, 99–102 (Nov. 1990) (U.S. Patent and Trademark Office, Office of the Assistant Commissioner for Patents, Washington, D.C. 20231); *Genes and Genomes*, Singer & Berg (Eds.), University Science Books, Mill Valley, Calif, 1991, at p. 60.

As used herein, "ligand" refers to a molecule that is recognized by a particular receptor protein. With reference to the present invention, a CTD kinase ligand is a molecule, such as a peptide, that is bound by CTD kinase. As used herein, an "inhibitory ligand" or an "inhibitory binding ligand" is a ligand which binds to and inhibits the normal activity of the receptor protein. "Receptor" refers to a molecule that has an affinity for a given ligand.

As used herein, the term "parasite" refers to an organism that must reside in a host organism during at least some portion of its life, in order to complete its life cycle. As used herein, "protozoan parasite" refers to single-celled parasites, including but not limited to Sporozoa (the class of protozoans which includes the genera Plasmodium, Eimeria, Isospora and Toxoplasma). The genus Plasmodium includes species which are the causal agents of malaria in humans and other mammalian hosts. Malaria in humans is caused, for example, by *P. falciparum, P. vivax, P. malariae, P. ovale, P. tenue,* and variants of these species. Other Plasmodium species include *P. berghei* (found primarily in rodents) and *P. kochi* and *P. pitheci* (found primarily in monkeys and apes). Monkeys and apes infected with Plasmodium species have been used experimentally as animal models for human malaria; *P. berghei* allows the use of rodents as animal models. The protozoan family Trypanosomatidae (class Zoomastiga, order Kinetoplastida) includes the genera Leishmania and Trypanosoma. Pathogenic forms of Trypanosoma cause trypanosomiasis in man as well as a number of other diseases in domestic animals. *T. cruzi* causes Chagas' disease in man; dog, cats, rats and certain monkeys can also be infected with *T. cruzi*.

Multiple forms and stages of a parasite may be present within a host (e.g., cysts, gametocytes, trophozooites, etc.), and it will be understood by one skilled in the art that the present invention as directed to detection or treatment will appertain to those forms of the parasite which require active CTD kinase.

As used herein, CTD refers to the carboxyl-terminal repeat domain of the largest subunit of RNA polymerase II as found, for example, in mammals, yeast, Drosophila and protozoans.

A. CTD Kinase

The CTD region is reported as essential for viability, as yeast or mouse cells containing RNA polymerase II from which all or most of the repeats have been removed do not grow. Allison et al, *Mol. Cell Biol.,* 8, 321 (1988); Nonet, Sweetser & Young, *Cell,* 50, 909 (1987); Bartolomei, *Mol. Cell. Biol.,* 8, 330 (1988); Zehring et al, *Proc. Natl. Acad. Sci.,* 85, 3698 (1988). The hyperphosphorylation of CTD is thought to play an important role in initiating transcription and in other aspects of RNA polymerase II function (see Weeks et al., *Genes & Development* 7, 2329–2344 (December 1993)).

A protein kinase that hyperphosphorylates the CTD of human RNA polymerase II has been identified from the yeast *Saccharomyces cerevisiae,* and has been purified and characterized. Lee and Greenleaf, *Proc. Natl. Acad. Sci. USA* 86, 3624–3628, (1989). The CTD of *Saccharomyces cerevisiae* RNA polymerase II closely resembles that of mammals except that it is shorter (26 repeats of the heptamer Tyr-Ser-Pro-Thr-Ser-Pro-Ser (SEQ ID NO:1), rather than 52 repeats as in humans). Using bacterially produced CTD-containing fusion proteins as substrates, it has been shown that the yeast CTD kinase can efficiently hyperphosphorylate human CTD, and conversely, a similar kinase activity in human cell extracts hyperphosphorylates yeast CTD. Lee and Greenleaf, *Proc. Natl. Acad. Sci. USA,* 86, 3624 (1989). In both cases, a characteristic feature of the CTD kinase activity was the marked mobility shift induced in the substrate fusion proteins upon phosphorylation. It has also been shown that mammalian CTD can functionally replace yeast CTD in living yeast cells (see Allison et al., *Mol. Cell. Biol.,* 8, 321–329 (1988)).

Additional CTD kinases that have been purified are a template-associated protein kinase from HeLa cells (Dvir et al., *J. Biol. Chem.,* 268, 10440 (1993)), CTD kinases KI, KII and KIII from Aspergillis (Stone and Reinberg, *J. Biol. Chem.,* 267, 6353 (1992)), kinases CTDK1 and CTDK2 from HeLa cells (Payne and Dahmus, *J. Biol. Chem.,* 268, 80 (1993)), and cdc2-containing CTD kinases E1 and E2 from mouse (Zhang and Corden, *J. Biol. Chem.,* 266, 2290 (1991)). Human general transcription factor IIH is reported to phosphorylate the C-terminal domain of RNA polymerase II (Lu et al., *Nature,* 358, 641 (1992), and yeast RNA polymerase II transcription factor b appears to be associated with CTD kinase (Gileadi et al, *Science,* 257, 1389 (1992). Other CTD kinase activities have been identified in extracts from mammalian (Stevens and Maupin, *Biochem. Biophys. Res. Commun.,* 159, 508 (1989); Legagneux et al., *Eur. J. Biochem.,* 193, 121 (1990)) and plant cells (Guilfoyle, *Plant Cell,* 1, 827 (1989)).

The gene for the largest, catalytic subunit of the yeast CTD kinase (CTK1) has been cloned, sequenced and manipulated. The CTK1 protein was found to be a member of the cdc2 kinase family, and its protein kinase-homologous domain exhibited approximately 40% identity with known cdc2 proteins, including *S. cerevisiae* CDC28. It has been shown that CTD kinase is essential for normal growth of cells; furthermore, in cells with a mutated ctk1 gene, the CTD of the Pol II largest subunit is abnormally phosphorylated (Lee and Greenleaf, *Gene. Expr.* 1, 149–167, (1991)).

The nucleotide and predicted amino acid sequences of the *Plasmodium falciparum* RPII gene, including the CTD, are given in Li et al., *Nucleic Acids Res.* 17, 9621–9636 (1989). The CTD sequences of *Plasmodium falciparum* and *Plas-*

*modium berghei* are compared in Giesecke et al., *Biochem. Biophys. Res. Commun.* 180, 1350–1355 (1991). The CTD of *P. vivax* has been sequenced and found to be similar to that of *P. falciparum* (J. M. Lee, unpublished data, 1994). The Plasmodium CTD contains a variant of the human repeat heptad (Tyr-Ser-Pro-Thr-Ser-Pro-Ser (SEQ ID NO:1)), having a Lysine residue in place of the final Serine residue (Tyr-Ser-Pro-Thr-Ser-Pro-Lys (SEQ ID NO:2)). Because each repeat contains a Lys residue, the Plasmodium CTD is a highly positively charged entity. This contrasts to the relatively uncharged nature of yeast, Drosophila and mammalian CTDs.

The RNA polymerase II of certain other protozoan parasites in addition to Plasmodium are known or suspected to contain C-terminal repeat domains. Toxoplasma species and coccidia (i.e., members of the order Coccidia) such as Eimeria and Isospora are taxonomically the closest relatives of Plasmodium, and therefore would be expected by those in the art to contain CTDs.

Other parasitic protozoans contain a C-terminal extension (CTE) domain, rather than a CTD domain. CTE domains contain a single amino acid sequence rather than repeating amino acid sequences, and are rich in phosphorylatable residues. The largest subunit of *Trypanosoma brucei* RNA polymerase II, for example, has a carboxy-terminus extension (CTE) consisting of 228 amino acids and rich in serine and proline. Evers et al., *Cell,* 56, 585 (1989); Smith et al, *Cell,* 56, 815 (1989). The CTE of *Schistosoma mansoni* has been sequenced and found to contain a multiplicity of phosphorylatable residues (J. M. Lee, unpublished data, 1994). While the phosphorylatable area of a repeating domain is more readily apparent due to the repetition in sequence, using techniques known in the art the phosphorylatable area of a CTE domain and the peptide substrate can be determined. For example, once the sequence of a given CTE region is determined and an associated CTE kinase identified, a peptide library or other combinatorial library could be screened to find peptide substrates and inhibitors of the CTE kinase.

The present invention is based on the identification of the CTD kinase of *Plasmodium falciparum* and the discovery that Plasmodium CTD kinase displays a specificity distinct from the analogous activity in human cells. The specificity differences between parasite and host CTD kinases can be used to design selective peptide or peptide mimetic inhibitors of the CTD kinase of parasites such as Plasmodium species and other sporozoan CTD kinase. Such inhibitors function as pharmacological inhibitors of CTD phosphorylation, and thus as anti-parasitic, and particularly anti-malarial, agents. The identification of distinct CTD kinase specificity in other parasite-host paris will likewise lead to the design of CTD kinase inhibitors directed to the given parasite, for use in anti-parasite treatments and in diagnosis.

B. Inhibitory Analogs and Mimetics

Analogs of CTD kinase ligands are an aspect of the present invention. As used herein, an "analog" is a chemical compound similar in structure to a first compound, and having either a similar or opposite physiologic action as the first compound. With particular reference to the present invention, CTD kinase ligand analogs are those compounds which, while not having the amino acid sequences of native CTD ligands, are capable of binding to CTD kinase. Such analogs may be peptide or non-peptide analogs, including nucleic acid analogs, as described in further detail below.

The regular spacing of proline residues is highly conserved among CTDs of various species. Due to the repetitiveness and the high proline content of the CTD, it is predicted that the CTD adopts an unusual conformation. Several potential secondary structures have been proposed on the basis of modeling studies. See Matsushima, Creutz and Kretsinger, *Proteins,* 7, 125–155 (1990).

In protein molecules which interact with a receptor, the interaction between the protein and the receptor must take place at surface-accessible sites in a stable three-dimensional molecule. By arranging the critical binding site residues in an appropriate conformation, peptides which mimic the essential surface features of the present RNA polymerase CTD regions may be designed and synthesized in accordance with known techniques.

Methods for determining peptide three-dimensional structure and analogs thereto are known, and are sometimes referred to as "rational drug design techniques". See, e.g., U.S. Pat. No. 4,833,092 to Geysen; U.S. Pat. No. 4,859,765 to Nestor; U.S. Pat. No. 4,853,871 to Pantoliano; U.S. Pat. No. 4,863,857 to Blalock; (applicants specifically intend that the disclosures of all U.S. Patent references cited herein be incorporated by reference herein in their entirety). See also Waldrop, *Science,* 247, 28029 (1990); Rossmann, *Nature,* 333, 392–393 (1988); Weis et al., *Nature,* 333, 426–431 (1988); James et al., *Science,* 260, 1937 (1993) (development of benzodiazepine peptidomimetic compounds based on the structure and function of tetrapeptide ligands).

In general, those skilled in the art will appreciate that minor deletions or substitutions may be made to the amino acid sequences of peptides of the present invention without unduly adversely affecting the activity thereof. Thus, peptides containing such deletions or substitutions are a further aspect of the present invention. In peptides containing substitutions or replacements of amino acids, one or more amino acids of a peptide sequence may be replaced by one or more other amino acids wherein such replacement does not affect the function of that sequence. Such changes can be guided by known similarities between amino acids in physical features such as charge density, hydrophobicity/hydrophilicity, size and configuration, so that amino acids are substituted with other amino acids having essentially the same functional properties. For example: Ala may be replaced with Val or Ser; Val may be replaced with Ala, Leu, Met, or Ile, preferably Ala or Leu; Leu may be replaced with Ala, Val or Ile, preferably Val or Ile; Gly may be replaced with Pro or Cys, preferably Pro; Pro may be replaced with Gly, Cys, Ser, or Met, preferably Gly, Cys, or Ser; Cys may be replaced with Gly, Pro, Ser, or Met, preferably Pro or Met; Met may be replaced with Pro or Cys, preferably Cys; His may be replaced with Phe or Gln, preferably Phe; Phe may be replaced with His, Tyr, or Trp, preferably His or Tyr; Tyr may be replaced with His, Phe or Trp, preferably Phe or Trp; Trp may be replaced with Phe or Tyr, preferably Tyr; Asn may be replaced with Gln or Ser, preferably Gln; Gln may be replaced with His, Lys, Glu, Asn, or Ser, preferably Asn or Ser; Ser may be replaced with Gln, Thr, Pro, Cys or Ala; Thr may be replaced with Gln or Ser, preferably Ser; Lys may be replaced with Gln or Arg; Arg may be replaced with Lys, Asp or Glu, preferably Lys or Asp; Asp may be replaced with Lys, Arg, or Glu, preferably Arg or Glu; and Glu may be replaced with Arg or Asp, preferably Asp. Once made, changes can be routinely screened to determine their effects on function with enzymes.

Non-peptide mimetics of the peptides of the present invention are also an aspect of this invention. Non-protein drug design may be carried out using computer graphic modeling to design non-peptide, organic molecules able to bind to CTD kinase. See, e.g., Knight, *BIO/Technology,* 8, 105 (1990). Itzstein et al, *Nature,* 363, 418 (1993) (peptidomimetic inhibitors of influenza virus enzyme, sialidase). Itzstein et al modeled the crystal structure of the sialidase receptor protein using data from x-ray crystallography studies and developed an inhibitor that would attach to active sites of the model; the use of nuclear magnetic resonance (NMR) data for modeling is also known in the art. See also Lam et al, *Science*, 263, 380 (Jan. 1994) regarding the rational design of bioavailable nonpeptide cyclic ureas that function as HIV protease inhibitors. Lam et al used information from x-ray crystal structure studies of HIV protease inhibitor complexes to design nonpeptide inhibitors.

The modeling of a protein kinase structure using the known structure of other kinases is reported by Knighton et al., *Science*, 258, 130 (1992) (smooth muscle myosin light chain kinase catalytic core modeled using crystallography data of cyclic AMP-dependent protein kinase catalytic subunit and a bound pseudosubstrate inhibitor). See also Marcote et al., *Mol. Cell. Biol.*, 13, 5122 (1993) (crystallography data of cyclic AMP dependent protein kinase used to model Cdc2 protein kinase); Knighton et al., *Science*, 253, 407 (1991); Knighton et al., *Science*, 253, 414 (1991); DeBondt et al., *Nature*, 363, 595 (1993) (crystal structure of human CDK2 kinase determined).

Analogs may also be developed by generating a library of molecules, selecting for those molecules which act as ligands for a specified target, and identifying and amplifying the selected ligands. See, e.g., Kohl et al., *Science*, 260, 1934 (1993) (synthesis and screening of tetrapeptides for inhibitors of farnesyl protein transferase, to inhibit ras oncoprotein dependent cell transformation). Techniques for constructing and screening combinatorial libraries of oligomeric biomolecules to identify those that specifically bind to a given receptor protein are known. Suitable oligomers include peptides, oligonucleotides, carbohydrates, nonoligonucleotides (e.g., phosphorothioate oligonucleotides; see *Chem. and Engineering News*, page 20, 7 Feb. 1994) and nonpeptide polymers ( see, e.g., "peptoids" of Simon et al., *Proc. Natl. Acad. Sci. USA*, 89, 9367 (1992)). See also U.S. Pat. No. 5,270,170 to Schatz; Scott and Smith, *Science*, 249, 386–390 (1990); Devlin et al., *Science* 249, 404–406 (1990); Edgington, *BIO/Technology*, 11, 285 (1993). Peptide libraries may be synthesized on solid supports, or expressed on the surface of bacteriophage viruses (phage display libraries). Known screening methods may be used by those skilled in the art to screen combinatorial libraries to identify CTD kinase ligands. Techniques are known in the art for screening synthesized molecules to select those with the desired activity, and for labelling the members of the library so that selected active molecules may be identified. See, e.g., Brenner and Lerner, *Proc. Natl. Acad. Sci. USA*, 89, 5381 (1992) (use of genetic tag to label molecules in a combinatorial library); PCT US93/06948 to Berger et al., (use of recombinant cell transformed with viral transactivating element to screen for potential antiviral molecules able to inhibit initiation of vital transcription); Simon et al., *Proc. Natl. Acad. Sci. USA*, 89, 9367, (1992) (generation and screening of "peptoids", oligomeric N-substituted glycines, to identify ligands for biological receptors); U.S. Pat. No. 5,283,173 to Fields et al., (use of genetically altered *Saccharomyces cerevisiae* to screen peptides for interactions).

As used herein, "combinatorial library" refers to collections of diverse oligomeric biomolecules of differing sequence, which can be screened simultaneously for activity as a ligand for a particular target. Combinatorial libraries may also be referred to as "shape libraries", i.e., a population of randomized polymers which are potential ligands. The shape of a molecule refers to those features of a molecule that govern its interactions with other molecules, including Van der Waals, hydrophobic, electrostatic and dynamic.

Nucleic acid molecules may also act as ligands for receptor proteins. See, e.g., Edgington, *BIO/Technology*, 11, 285 (1993). U.S. Pat. No. 5,270,163 to Gold and Tuerk describes a method for identifying nucleic acid ligands for a given target molecule by selecting from a library of RNA molecules with randomized sequences those molecules that bind specifically to the target molecule. A method for the in vitro selection of RNA molecules immunologically cross-reactive with a specific peptide is disclosed in Tsai, Kenan and Keene, *Proc. Natl. Acad. Sci. USA*, 89, 8864 (1992) and Tsai and Keene, *J. Immunology*, 150, 1137 (1993). In the method, an antiserum raised against a peptide is used to select RNA molecules from a library of RNA molecules; selected RNA molecules and the peptide compete for antibody binding, indicating that the RNA epitope functions as a specific inhibitor of the antibody-antigen interaction.

C. Proteins and Peptides

The term CTD kinase "substrate equivalent" as used herein refers to proteins or peptides that bind CTD kinase and are phosphorylated in a manner similar to native CTD regions. These substrate equivalents may be fusion proteins containing the CTD region or may be formed by modifying the reactive groups within the substrate molecule's natural amino acid sequence or modifying the N-terminal amino and/or the C-terminal carboxyl group, and include salts formed with acids and/or bases, particularly physiologically acceptable inorganic and organic acids and bases. A particular embodiment is a peptide containing repeats of the consensus heptamer of the CTD region, or analogs of the consensus repeat which retain the ability to bind CTD kinase. Also included are substrate molecules with modified carboxyl and/or amino groups on the substrate to produce esters or amides, or amino acid protecting groups such as N-t-butoxycarbonyl. Preferred modifications are those which provide a more stable, active peptide which will be less prone to enzymatic degradation in vivo. It will be appreciated by one skilled in the art that a "substrate equivalent" may also function as an "inhibitory ligand" as described above, as a molecule which binds to CTD kinase will competitively inhibit the binding of RNA polymerase CTD regions with the CTD kinase receptor. The present invention encompasses peptides and analogs which bind to the CTD kinase and are phosphorylated by the enzyme, as well as those which bind but are not phosphorylated.

The proteins and peptides of the invention may be made in accordance with techniques known in the art. Using accepted techniques of chemical synthesis, the peptide is built up either from the N-terminus or, more typically, the C-terminus using either single amino acids or preformed peptides containing two or more amino acid residues. Particular techniques for synthesizing peptides include (a) classical methods in which peptides of increasing size are isolated before each amino acid or preformed peptide addition, and (b) solid phase peptide synthesis in which the peptide is built up attached to a resin such as a Merrifield resin. In these synthetic procedures, groups on the amino acids will generally be in protected form using standard protecting groups such as t-butoxycarbonyl. If necessary, these protecting groups are cleaved once the synthesis is complete. Other modifications may be introduced during or after the synthesis of the peptide.

Peptides and fusion proteins of the present invention may also be produced through recombinant DNA procedures. Nucleotide sequences for DNA sequences which code for peptides or fusion proteins of the present invention (useful as intermediates for making the same) can be determined with any table setting forth the genetic code. See, e.g., R. Old and S. Primrose, Principles of Gene Manipulation, 346 (3d ed. 1985).

The peptides of the present invention include peptides consisting of repeats of short amino acid sequences. The number of repeats in a peptide will depend on its intended use. In general, peptides intended for in vivo use will consist of up to about twenty-five repeats of an amino acid sequence of about ten or fewer amino acids. Peptides intended for in vitro use may consist of any number of repeats, such as up to about 100 repeats of an amino acid sequence of about ten or fewer amino acids.

The production of recombinant DNA, vectors, host cells, and proteins by genetic engineering techniques is well known. See, e.g., U.S. Pat. No. 4,761,371 to Bell et al. at Col. 6 line 3 to Col. 9 line 65; U.S. Pat. No. 4,877,729 to Clark et al. at Col. 4 line 38 to Col. 7 line 6; U.S. Pat. No. 4,912,038 to Schilling at Col. 3 line 26 to Col. 14 line 12; and U.S. Pat. No. 4,879,224 to Wallner at Col. 6 line 8 to Col. 8 line 59. (Applicants specifically intend that the disclosures of all U.S. Patent references cited herein be incorporated by reference herein in their entirety).

DNA sequences encoding desired proteins may be recovered by use of the polymerase chain reaction (PCR) procedure and splicing by overlap extension (SOE), as is known in the art. See U.S. Pat. Nos. 4,683,195 to Mullis et al. and 4,683,202 to Mullis.

The proteins may be synthesized in host cells transformed with vectors containing DNA encoding the proteins. A vector is a replicable DNA construct. Vectors are used herein either to amplify DNA encoding the protein and/or to express DNA which encodes the protein. An expression vector is a replicable DNA construct in which a DNA sequence encoding the protein is operably linked to suitable control sequences capable of effecting the expression of the protein in a suitable host. The need for such control sequences will vary depending upon the host selected and the transformation method chosen. Generally, control sequences include a transcriptional promoter, an optional operator sequence to control transcription, a sequence encoding suitable mRNA ribosomal binding sites, and sequences which control the termination of transcription and translation. Amplification vectors do not require expression control domains. All that is needed is the ability to replicate in a host, usually conferred by an origin of replication, and a selection gene to facilitate recognition of transformants.

Vectors useful for practicing the present invention include plasmids, viruses (including phage), retroviruses, and integratable DNA fragments (i.e., fragments integratable into the host genome by homologous recombination). The vector replicates and functions independently of the host genome, or may, in some instances, integrate into the genome itself. Suitable vectors will contain replicon and control sequences which are derived from species compatible with the intended expression host. Transformed host cells are cells which have been transformed or transfected with the protein vectors constructed using recombinant DNA techniques. Transformed host cells ordinarily express the protein, but host cells transformed for purposes of cloning or amplifying the protein DNA need not express the protein.

DNA regions are operably linked when they are functionally related to each other. For example: a promoter is operably linked to a coding sequence if it controls the transcription of the sequence; a ribosome binding site is operably linked to a coding sequence if it is positioned so as to permit translation. Generally, operably linked means contiguous and, in the case of leader sequences, contiguous and in reading phase.

Suitable host cells include prokaryotes, yeast cells or higher eukaryotic cells. Prokaryotes include gram negative or gram positive organisms, for example *Escherichia coli* (*E. coli*) or Bacilli. Higher eukaryotic cells include established cell lines of mammalian origin as described below. Exemplary host cells are *E. coli* W3110 (ATCC 27,325), *E. coli* B, *E. coli* X1776 (ATCC 31,537), and *E. coli* 294 (ATCC 31,446). Pseudomonas species, Bacillus species, and *Serratia marcesans* are also suitable.

A broad variety of suitable microbial vectors are available. Generally, a microbial vector will contain an origin of replication recognized by the intended host, a promoter which will function in the host and a phenotypic selection gene such as a gene encoding proteins conferring antibiotic resistance or supplying an autotrophic requirement. Similar constructs will be manufactured for other hosts. *E. coli* is typically transformed using pBR322. See Bolivar et al., *Gene* 2, 95 (1977). pBR322 contains genes for ampicillin and tetracycline resistance and thus provides easy means for identifying transformed cells.

Expression vectors should contain a promoter which is recognized by the host organism. This generally means a promoter obtained from the intended host. Promoters most commonly used in recombinant microbial expression vectors include the beta-lactamase (penicillinase) and lactose promoter systems (Chang et al., *Nature* 275, 615 (1978); and Goeddel et al., *Nature* 281, 544 (1979)), a tryptophan (trp) promoter system (Goeddel et al., *Nucleic Acids Res.* 8, 4057 (1980) and EPO App. Publ. No. 36,776) and the tac promoter (H. De Boer et al., *Proc. Natl. Acad. Sci. USA* 80, 21 (1983)). While these are commonly used, other microbial promoters are suitable. Details concerning nucleotide sequences of many have been published, enabling a skilled worker to operably ligate them to DNA encoding the protein in plasmid or viral vectors (Siebenlist et al., *Cell* 20, 269 (1980)). The promoter and Shine-Dalgarno sequence (for prokaryotic host expression) are operably linked to the DNA encoding the desired protein, i.e., they are positioned so as to promote transcription of the protein messenger RNA from the DNA.

Eukaryotic microbes such as yeast cultures may be transformed with suitable protein-encoding vectors. See, e.g., U.S. Pat. No. 4,745,057. *Saccharomyces cerevisiae* is the most commonly used among lower eukaryotic host microorganisms, although a number of other strains are commonly available. Yeast vectors may contain an origin of replication from the 2 micron yeast plasmid or an autonomously replicating sequence (ARS), a promoter, DNA encoding the desired protein, sequences for polyadenylation and transcription termination, and a selection gene. An exemplary plasmid is YRp7, (Stinchcomb et al., *Nature* 282, 39 (1979); Kingsman et al., *Gene* 7, 141 (1979); Tschemper et al., *Gene* 10, 157 (1980)). This plasmid contains the trpl gene, which provides a selection marker for a mutant strain of yeast lacking the ability to grow in tryptophan, for example ATCC No. 44076 or PEP4-1 (Jones, *Genetics* 85, 12 (1977)). The presence of the trpl lesion in the yeast host cell genome then provides an effective environment for detecting transformation by growth in the absence of tryptophan.

Suitable promoting sequences in yeast vectors include the promoters for metallothionein, 3-phosphoglycerate kinase (Hitzeman et al., *J. Biol. Chem.* 255, 2073 (1980) or other glycolytic enzymes (Hess et al., *J. Adv. Enzyme Reg.* 7, 149 (1968); and Holland et al., *Biochemistry* 17, 4900 (1978)), such as enolase, glyceral-dehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Suitable vectors and promoters for use in yeast expression are further described in R. Hitzeman et al., EPO Publn. No. 73,657.

Cultures of cells derived from multicellular organisms are a desirable host for recombinant protein synthesis. In principal, any higher eukaryotic cell culture is workable, whether from vertebrate or invertebrate culture, including insect cells. Propagation of such cells in cell culture has become a routine procedure. See Tissue Culture, Academic Press, Kruse and Patterson, editors (1973). Examples of useful host cell lines are VERO and HeLa cells, Chinese hamster ovary (CHO) cell lines, and WI138, BHK, COS-7, CV, and MDCK cell lines. Expression vectors for such cells ordinarily include (if necessary) an origin of replication, a promoter located upstream from the gene to be expressed, along with a ribosome binding site, RNA splice site (if intron-containing genomic DNA is used), a polyadenylation site, and a transcriptional termination sequence.

The transcriptional and translational control sequences in expression vectors to be used in transforming vertebrate cells are often provided by viral sources. For example, commonly used promoters are derived from polyoma, Adenovirus 2, and Simian Virus 40 (SV40). See, e.g., U.S. Pat. No. 4,599,308. The early and late promoters are useful because both are obtained easily from the virus as a fragment which also contains the SV40 viral origin of replication. See Fiers et al., *Nature* 273, 113 (1978). Further, the protein promoter, control and/or signal sequences, may also be used, provided such control sequences are compatible with the host cell chosen.

An origin of replication may be provided either by construction of the vector to include an exogenous origin, such as may be derived from SV40 or other viral source (e.g. Polyoma, Adenovirus, VSV, or BPV), or may be provided by the host cell chromosomal replication mechanism. If the vector is integrated into the host cell chromosome, the latter may be sufficient.

Host cells such as insect cells (e.g., cultured *Spodoptera frugiperda* cells) and expression vectors such as the baculovirus expression vector (e.g., vectors derived from *Autographa californica* MNPV, *Trichoplusia ni* MNPV, Rachiplusia ou MNPV, or Galleria ou MNPV) may be employed in carrying out the present invention, as described in U.S. Pat. Nos. 4,745,051 and 4,879,236 to Smith et al. In general, a baculovirus expression vector comprises a baculovirus genome containing the gene to be expressed inserted into the polyhedrin gene at a position ranging from the polyhedrin transcriptional start signal to the ATG start site and under the transcriptional control of a baculovirus polyhedrin promoter.

Rather than using vectors which contain viral origins of replication, one can transform mammalian cells by the method of cotransformation with a selectable marker and the chimeric protein DNA. An example of a suitable selectable marker is dihydrofolate reductase (DHFR) or thymidine kinase. See U.S. Pat. No. 4,399,216. Such markers are proteins, generally enzymes, that enable the identification of transformant cells, i.e., cells which are competent to take up exogenous DNA. Generally, identification is by survival of transformants in culture medium that is toxic, or from which the cells cannot obtain critical nutrition without having taken up the marker protein.

D. Subjects

The molecules of the present invention are useful in inhibiting the CTD kinase activity (and hence the RNA polymerase II activity) of parasites, and may be used in treating hosts with parasitic infections where the activity of the host CTD kinase is distinct from that of the parasite. Potential hosts include both mammals and avians such as chickens. Particularly preferred as subjects are mammalian hosts with protozoan infections, and more particularly, mammalian hosts with sporozoan infections such as Plasmodium infections. The present invention may also be useful in treating infections by metazoan parasites, where the activity of the host CTD kinase is distinct from that of the metazoan parasite. Such metazoan parasites include, but are not limited to, parasites of the genera Schistosoma, Onchocerca, Loa and Dracunculus.

The peptides, fusion proteins and other molecules of the present invention may be prepared per se or in the form of pharmaceutically acceptable salts thereof. Pharmaceutically acceptable salts are those that retain the desired biological activity of the parent compound and do not impart undesired toxicological effects. For example, acid addition salts of acetate, adipate, alginate, aspartate, benzoate, benzenesulfonate, bisulfate, butyrate, citrate, camphorate, camphorsulfonate, cyclopentanepropionate, digluconate, dodecylsulfonate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylproprionate, picrate, pivalate, propionate, succinate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Molecules of the present invention may also be formulated to increase membrane permeability, such as by using lipid vesicle delivery systems, or by the incorporation of hydrophobic cleavable protective groups, as is known in the art.

Pharmaceutical formulations of the instant invention comprise the desired molecules in a pharmaceutically acceptable carrier, such as sterile, pyrogen-free water or sterile pyrogen-free phosphate-buffered saline solution. The molecules described above being the active ingredient in these compositions, they should be included in an amount effective to accomplish the intended treatment. The precise amount to be administered to a subject is determined in a routine manner, and will vary depending on the subject, condition being treated, severity of the condition, and route of administration. The effectiveness of a dosing regimen may be ascertained by measures known in the art, including but not limited to amelioration of clinical symptoms or laboratory signs, reduction in the number of parasites, and a decrease in the rate of increase or the rate of reproduction of the parasite. When used as an anti-parasite treatment, the molecules of the present invention may be used in conjunction with other anti-parasitic treatments.

For the preparation of these compositions, use can be made of pharmaceutical carriers adapted for all conventional forms of administration, for example, tablets, capsules, dragees, syrups, solutions, suspensions, aerosols and the like. As injection medium, it is preferred to use water which contains the additives usual in the case of injection solutions, such as stabilizing agents and/or buffers.

Any suitable route of administration may be employed in carrying out the methods of the present invention, including but not limited to oral administration, intranasal or inhalation administration, intravenous injection, intraarterial injection, intraperitoneal injection, intramuscular injection, and subcutaneous injection.

Subjects to be treated by the methods disclosed herein are preferably mammalian subjects, such as human, cat, dog, rodent and horse subjects. Thus the present invention has both medical and veterinary applications. As used herein, the term "combatting" or "treating" parasitic infections means decreasing the numbers of parasites present in the mammalian host tissues or blood over that which would occur without such treatment. This decrease may occur by killing one or more developmental stages of the parasite, suppressing replication of the parasite, or interfering with the maturation of the parasite in vivo. See, e.g., *Chemotherapy of Malaria*, 2d Edition, L. J. Bruce-Chwatt et al (eds.), (Chapter Two: Fundamental Aspects of Chemotherapy of Malaria), World Health Organization, Geneva (1986).

The present invention also provides a method to detect the presence of parasites in blood or other tissues from subjects, where the activities of the host and parasite CTD kinases are distinct. In such case, the hyperphosphorylation of parasite CTD kinase substrate equivalent in a sample of tissue indicates the presence of active CTD kinase of the parasite in question, and hence the presence of the parasite. Such a method can be used, for example, to test human blood for the presence of malarial parasites, or to test rodent blood for the presence of experimental *P. berghei* infections. The tissue type selected as the sample will vary depending on the parasite being assayed and the form of the parasite being assayed; the selection of tissue samples will be apparent to one skilled in the art. For example, blood samples may be assayed for the presence of Plasmodium parasites, while muscle tissue samples may be assayed for the presence of onchocercid parasites such as Onchocerca species. It will likewise be apparent to those skilled in the art that the sample may require treatment by known methods to make the parasite CTD kinase available to the added substrate; such treatments may include, for example, centrifugation, lysing of cells, and fractionation.

Further, the present invention provides a method of testing the susceptibility of Plasmodium parasites to an antimalarial drug. In clinical practice, failure of a subject to respond to drug treatment for Plasmodium infection may be due to inadequate dosage or to resistance of the parasite to the particular drug. Drug resistance varies among Plasmodium species and strains, and is a major factor in limiting the success of anti-malarial drug treatment. In vitro field tests for assessing drug resistance have been developed. For example, a test and a control sample of blood may be collected, and the test sample treated with the drug in question (for example, chloroquine). Because the maturation of susceptible parasites in vitro is inhibited by drugs such as chloroquine, the extent of inhibition caused by the drug is assessed by comparing the degree of maturation in the two samples. See *Chemotherapy of Malaria*, 2d Edition, L. J. Bruce-Chwatt et al (eds.), (Chapter Five: Drug Resistance in Malaria; Annex 6, In Vitro Tests for Susceptibility of *P. falciparum* to Chloroquine and Mefloquine), World Health Organization, Geneva (1986). Using the present invention, an exemplary method comprises collecting a test blood sample and a control blood sample from a mammalian subject infected with a Plasmodium parasite, contacting the test blood sample with the anti-malarial drug in question, contacting both blood samples with a sporozoan CTD kinase substrate equivalent and a source of phosphorus, and detecting and comparing the hyperphosphorylation of the substrate peptide in the blood samples, where significantly decreased hyperphosphorylation in the test sample indicates that the parasite is susceptible to the test drug.

Further, the present invention provides a method for determining whether a given host-parasite combination is amenable to anti-parasite treatment using CTD kinase inhibitors. In this method, the CTD regions on the host and the parasite RNA polymerase II are identified, and the CTD kinases which act to hyperphosphorylate these CTD regions are also identified. It is then determined whether the two CTD kinases have distinct specificities, such that parasite CTD kinase inhibitors will inhibit the parasite CTD kinase, but will not appreciably inhibit the host CTD kinase.

Where detection of hyperphosphorylation of CTD regions is employed in the present methods, any suitable source of phosphorus may be used, including phosphate donors such as adenosine triphosphate (ATP), uridine triphosphate (UTP), guanosine triphosphate (GTP), cytidine triphosphate (CTP), adenosine diphosphate (ADP), uridine diphosphate (UDP), guanosine diphosphate (GDP), and cytidine diphosphate (CDP). To facilitate the detection of hyperphosphorylation the phosphorus molecule may be labelled by methods known in the art, including the use of radiolabelled phosphorus.

Further, the present invention provides a method for screening for anti-parasite compounds effective in anti-parasite treatment for a known host-parasite combination, where the CTD kinase of the parasite has a specificity distinct from that of the host CTD kinase. The parasite CTD kinase is isolated and a combinatorial library is screen for molecules which bind to the parasite CTD kinase. The structures of these ligands are then determined, and the ligands are screened using assay procedures known in the art to determine those which inhibit the parasite CTD kinase but which do not appreciably inhibit the host CTD kinase. The combination libraries may comprise peptides, oligonucleotides, "peptoids," or other non-peptide molecules.

The following examples are provided to illustrate the present invention, and should not be construed as limiting thereof. In these examples, CTD means carboxy terminal domain; hCTD indicates a fusion protein carrying precise repeats of the human CTD; pCTD indicates a fusion protein carrying precise repeats of the plasmodium CTD; GST means glutathione-S-transferase; MBP means maltose binding protein; PMSF means phenylmethylsulfonyl fluoride; μCi means microCurie; μl means microliter; ml means milliliter; μM means microMolar; mM means milli Molar; mg means milligram; PAGE means polyacrylamide gel electrophoresis; kBq means kilo Bequerel.

EXAMPLE 1

Production of Fusion Proteins

Fusion protein constructs that carried a CTD region composed of precise repeats of either the human-or Plasmodium-type CTD were designed, and are hereinafter referred to hCTD and pCTD, respectively. Synthetic oligonucleotides encoding the respective CTDs were polymerized and cloned into expression vectors based on beta-galactosidase, glutathione-S-transferase (GST), or maltose binding protein (MBP), as is known in the art. See, e.g., Ruther and Muller-Hill, *EMBO J*, 2, 1791 (1983), Smith and Johnson, *Gene*, 67, 31 (1988); Maina et al, *Gene*, 74, 365 (1988). See also Lee and Greenleaf, *Proc. Natl. Acad. Sci. USA*, 86, 3624 (1989) (production of yeast CTD fusion proteins); and Lee J. M., *A protein kinase that phosphorylates the C-terminal repeat domain of the largest subunit of*

*RNA polymerase II*, Ph.D. Thesis, Department of Biochemistry, Duke University, Durham, N.C. (1989). Each was then expressed as a fusion protein in *Escherichia coli* and purified, according to techniques known in the art. The resulting fusion proteins were used as a CTD kinase substrate. The fusion proteins are termed, for example, MBP-hCTD for maltose binding protein/human CTD fusion protein.

To produce fusion proteins containing precise repeats of a heptamer the process described in Lee J. M., Ph.D. Thesis, Department of Biochemistry, Duke University, Durham, N.C. (1989), 44–46, was used. For example, to produce a beta-galactosidase fusion protein containing the peptide (Tyr-Ser-Pro-Thr-Ser-Pro-Ser)$_n$ (SEQ ID NO:1), two oligonucleotides were synthesized for one repeat of the heptamer sequence and a self ligation strategy was employed as described in Lee. High frequency codons of *E. coli* were chosen for each amino acid (Grantham et al., 1981), and arranged to both make them in-frame with beta-galactosidase of plasmid pUR290 and to introduce a stop codon at the end of the repeats. The two oligonucleotides were mixed, kinased by polynucleotide kinase, and ligated by standard procedures (see, e.g., Maniatis et al., *Molecular Cloning: A Laboratory Manual*, Cold Spring Harbor Laboratory, Cold Spring Harbor, N. Y. (1982)). Self-ligated DNA was selected for length using a nondenaturing polyacrylamide gel. The ends of DNA were made flush by filling with Klenow enzyme. The plasmid pUR290 was cut with BamHI, filled-in with Klenow enzyme, and the two DNAs were mixed and ligated. After transformation into *E. coli*, colonies were screened for fusion protein production. The fusion protein (betaGal-hCTD) was purified as described in Lee (Ph.D. Thesis, Department of Biochemistry, Duke University, Durham, N.C. (1989), chapter II). To construct the corresponding MBP-hCTD fusion protein, the DNA fragment encoding the repeats was subcloned (in frame with MBP) into plasmid pMALcR1 (New England Biolabs pMAL system; see also Maina et al., *Gene*, 74, 365 (1988)). This and other MBP fusion proteins were purified using an amylose column (New England Biolabs).

Fusion proteins with other repeat sequences (e.g., SEQ ID NO:2, SEQ ID NO:3, SEQ ID NO:4, SEQ ID NO:5, SEQ ID NO:6, and SEQ ID NO:7) were made similarly, using either the pMAL system for MBP fusions or the pGEX system for GST fusions (Pharmacia; and see Smith and Johnson, *Gene*, 67, 31 (1988)).

EXAMPLE 2

Assay of CTD Kinase Activity

Assay conditions were patterned after those described in Lee and Greenleaf, *Proc. Natl. Acad. Sci. USA* 86, 3624–3628 (1989), and Lee and Greenleaf, *Gene. Expr.* 1, 149–167, (1991). Analysis was by polyacrylamide gel electrophoresis and autoradiography, or by polyacrylamide gel electrophoresis and phosphorimager analysis.

Standard reaction mixtures (20 μl) contained fusion protein (final concentration of 0.15mg/ml for intact protein), Tris-HCl (25mM, pH 7.8), MgCl$_2$ (10 mM), NaF (5 mM), PMSF (1 mM), and [γ-$^{32}$P]ATP (300 μM, 1–3 μCi; 1 μCi=37 kBq). After incubation for 15 minutes at room temperature, reactions were terminated by the addition of NaDodSO$_4$ sample buffer. Phosphorylated products were analyzed by NaDodSO$_4$/6% PAGE followed by autoradiography.

EXAMPLE 3

Plasmodium CTD Kinase Activity

Plasmodium parasites were grown using the method of Trager and Jensen (Cultivation of erythrocytic and exoerythrocytic stages of Plasmodia, In *Malaria*, vol. 2, J. P. Kreier (Ed.), Academic Press, New York (1980)). Parasites were homogenized and separated into nuclear and cytoplasmic fractions. See Grall et al., *Exp. Parasitology*, 75, 10 (1992) (parasite isolation by percoll enrichment); Price et al., *J. Biol. Chem.*, 262, 3244 (1987) (preparation of nuclear extract); and Lee and Greenleaf, *Proc. Natl. Acad. Sci. USA*, 86, 3624 (1989) (purification of yeast kinase). Assays were conducted as described in Example 2, above.

Figure 1:
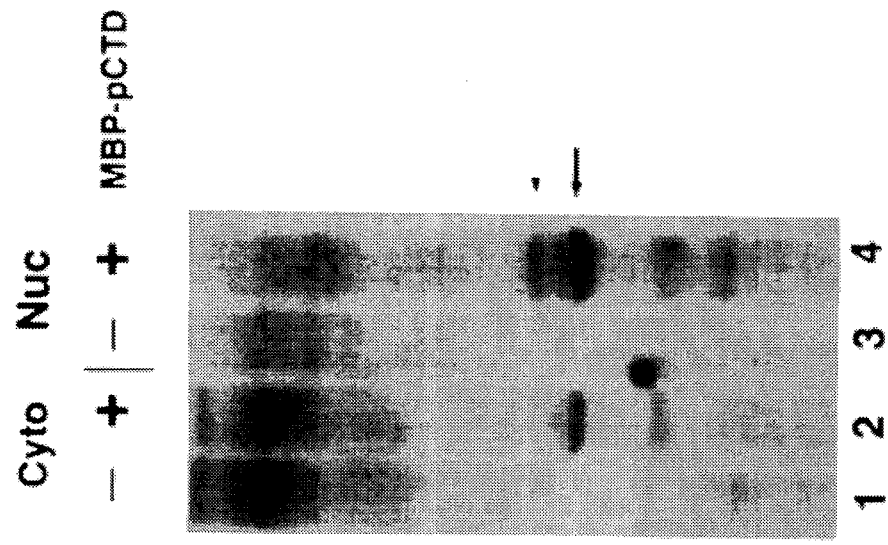
FIG. 1 is an autoradiogram using labelled phosphorus ($^{32}$P) to compare the phosphorylation of MBP-pCTD fusion protein by nuclear and cytoplasmic Plasmodium extracts.

Results are shown in FIG. 1, where lanes 1 and 2 contain cytoplasmic fraction, lanes 3 and 4 contain nuclear fractions; + indicates the presence of MBP-pCTD fusion protein (lanes 2 and 4) and − indicates the absence of the MBP-pCTD fusion protein (lanes 1 and 3). The nuclear extract contained a CTD kinase activity that generated a hyperphosphorylated, mobility-shifted MBP-pCTD fusion protein (FIG. 1, lane 4 at arrowhead); this is the kinase activity of interest. Activities that phosphorylate the fusion protein without causing a mobility shift are found in both the cytoplasmic and nuclear fractions (FIG. 1, lanes 2 and 4 at arrow). These activities may phosphorylate the MBP portion of the fusion protein or the CTD portion, but apparently at a low level. The intensity of the unshifted band is potentially misleading in the autoradiogram of FIG. 1 because only a small fraction of the fusion protein is shifted in mobility (stained gel, not shown); thus the $^{32}$P/protein ratio is much higher for the shifted band.

EXAMPLE 4

Plasmodium CTD Kinase Activity

The specificity of the Plasmodium CTD kinase was compared with that of a corresponding activity found in human (HeLa) cells. A Plasmodium extract was prepared from infected human blood cells (see *Mol. Biochem. Parasitolog*, 50, 17, 1992; see also *Blood*, 74, 471). This Plasmodium extract was thus contaminated with human proteins. The crude extract was partially fractionated by processing it through a phosphocellulose (P11, Whatman) column. Each fraction was assayed for activity and active fractions were pooled and applied to a DEAE-cellulose (DE52, Whatman) column. The enzyme was recovered and applied to a Mono S (FPLC, Pharmacia) column for further purification.

The purified extract was incubated with either the MBP-hCTD or the MBP-pCTD substrate as described in Example 2, above. Results are shown in FIG. 2, where lanes 1–3 contain Plasmodium extract, lanes 4–6 contain HeLa extract; lanes 1 and 4 had no fusion protein added, lanes 2 and 5 had MBP-hCTD added, and lanes 3 and 6 had MBP-pCTD added. The Plasmodium extract hyperphosphorylated the -pCTD substrate and generated a mobility-shifted product (FIG. 2, lane 3, at arrowhead). In contrast, the HeLa extract did not generate a mobility-shifted -pCTD product (FIG. 2, lane 6), although it did phosphorylate the fusion protein without causing a mobility shift (FIG. 2, arrow, "MBP-pCTD"). The HeLa extract contained, as expected, an activity that efficiently phosphorylated and shifted the MBP-hCTD substrate (FIG. 2, lane 5, upper arrowhead); this was the counterpart of the parasite activity of interest.

In experiments conducted essentially as described above, purified yeast enzyme also was active in mobility shifting the human-type CTD substrate, whereas no mobility shifting activity was detected toward the Plasmodium -type CTD (data not shown). The Plasmodium CTD did not substitute for the yeast CTD in vivo (J. Lee, unpublished data, data not shown).

In the Plasmodium extract used to produce FIG. 2, an activity was found that phosphorylated the —hCTD substrate and shifted its mobility (FIG. 2, lane 2, indicated by upper arrowhead on right margin). Because the experimental preparation used was significantly contaminated with human constituents, however, it was inferred that the mobility shift seen for the human-type CTD fusion protein in this experiment was due to contaminating human CTD kinase. This inference is supported by the next experiment.

EXAMPLE 5

Specificity of CTD Kinase Activity

Figure 3:
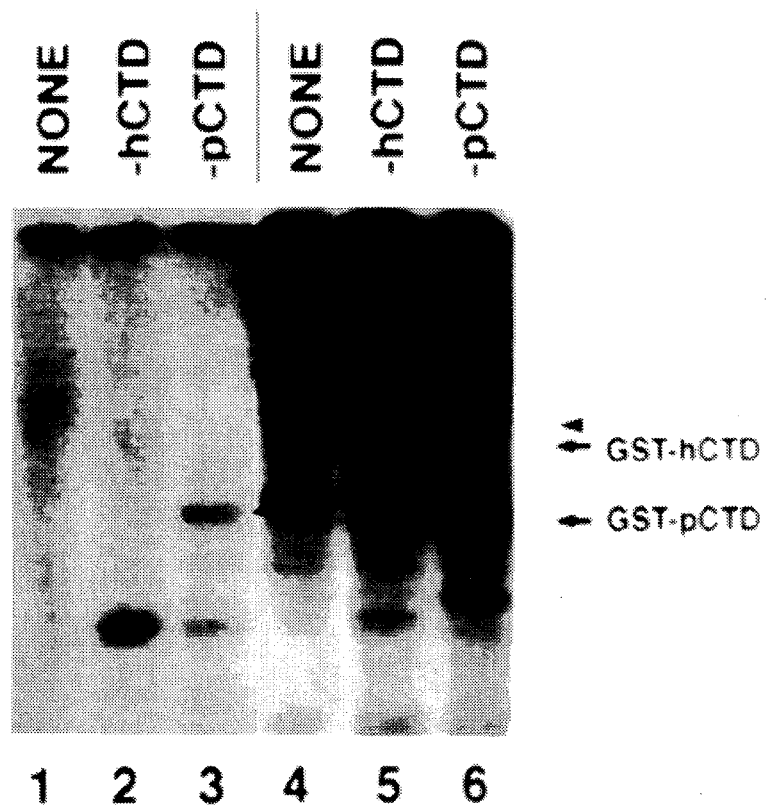
FIG. 3 is an autoradiogram comparing phosphorylation of the fusion proteins GST-hCTD and GST-pCTD by Plasmodium extract (from parasites) and HeLa cell extract.

The specificity of the CTD kinase activity was tested using a very pure sample of parasites as the starting material for extract preparation. See Choi & Mikkelson, *Exp. Parasitology*, 73, 93–100 (1991) for discussion of parasite purification; see Price, *J. Biol. Chem.* for details of extract preparation. CTD kinase was extracted as described in Example 3, above. Using this extract it was found that the Plasmodium enzyme has a substrate specificity distinct from that of the human enzyme as shown in FIG. 3 (where lanes 1–3 contained Plasmodium extract; 4–6 lanes contained HeLa extract; lanes 1 and 4 contained no fusion protein; lanes 2 and 5 contained GST-hCTD; lanes 3 and 6 contained GST-pCTD). The parasite CTD kinase activity mobility shifted a Plasmodium-type CTD substrate (FIG. 3, lane 3, arrowhead; unshifted position indicated by "GST-pCTD" at right margin), but did not phosphorylate a human-type substrate (FIG. 3, GST-hCTD, lane 2). A complementary specificity was displayed by HeLa extract, which phosphorylated and shifted the GST-hCTD fusion protein (FIG. 3, lane 5; arrowhead on right margin) but did not shift the GST-pCTD fusion protein (lane 6).

The above results indicate that the Plasmodium parasite and its human host contain distinct CTD kinases with selectivity for hyperphosphorylating the homologous CTD. By analogy with results demonstrating the essential nature of the yeast CTD kinase, it can be inferred that the Plasmodium CTD kinase is essential for normal growth of the parasite. Because the parasite enzyme has a specificity distinct from that of the human enzyme, the Plasmodium CTD kinase represents a pharmacological target in mammalian hosts.

EXAMPLE 6

Plasmodium CTD Kinase Inhibitors

Several fusion proteins with variant repeat domains as potential inhibitors of plasmodium CTD kinase were prepared and assayed. Positions in the repeats are referred to in accordance with sequence, numbered as follows:

$Tyr_1Ser_2Pro_3Thr_4Ser_5Pro_6Ser_7$ (SEQ ID NO:1)

As the difference in human CTD ($Ser_7$) and Plasmodium CTD ($Lys_7$), plays a role in determining Plasmodium CTD kinase specificity, derivatives based on the Plasmodium sequence Tyr-Ser-Pro-Thr-Ser-Pro-Lys (SEQ ID NO:2) were prepared and tested. The four repeat sequence analogs tested are shown in TABLE 1.

TABLE 1

| Consensus: | pCTD | (Tyr—Ser—Pro—Thr—Ser—Pro—Lys)n (SEQ ID NO: 2) |
|---|---|---|
| Analogs: | Name | Sequence |
| | A2 (SEQ ID NO: 3) | $(Tyr—Ala—Pro—Thr—Ser—Pro—Lys)_{13}$ |
| | A5 (SEQ ID NO: 4) | $(Tyr—Ser—Pro—Thr—Ala—Pro—Lys)_{13}$ |
| | A2A5 (SEQ ID NO: 5) | $(Tyr—Ala—Pro—Thr—Ala—Pro—Lys)_{13}$ |
| | R7 (SEQ ID NO: 6) | $(Tyr—Ser—Pro—Thr—Ser—Pro—Arg)_{13}$ |

Each analog was generated as a GST fusion protein with the repeats attached to the C-terminus of GST (as is known in the art) and were thus known as "GST-R7", etc.

Figure 4:
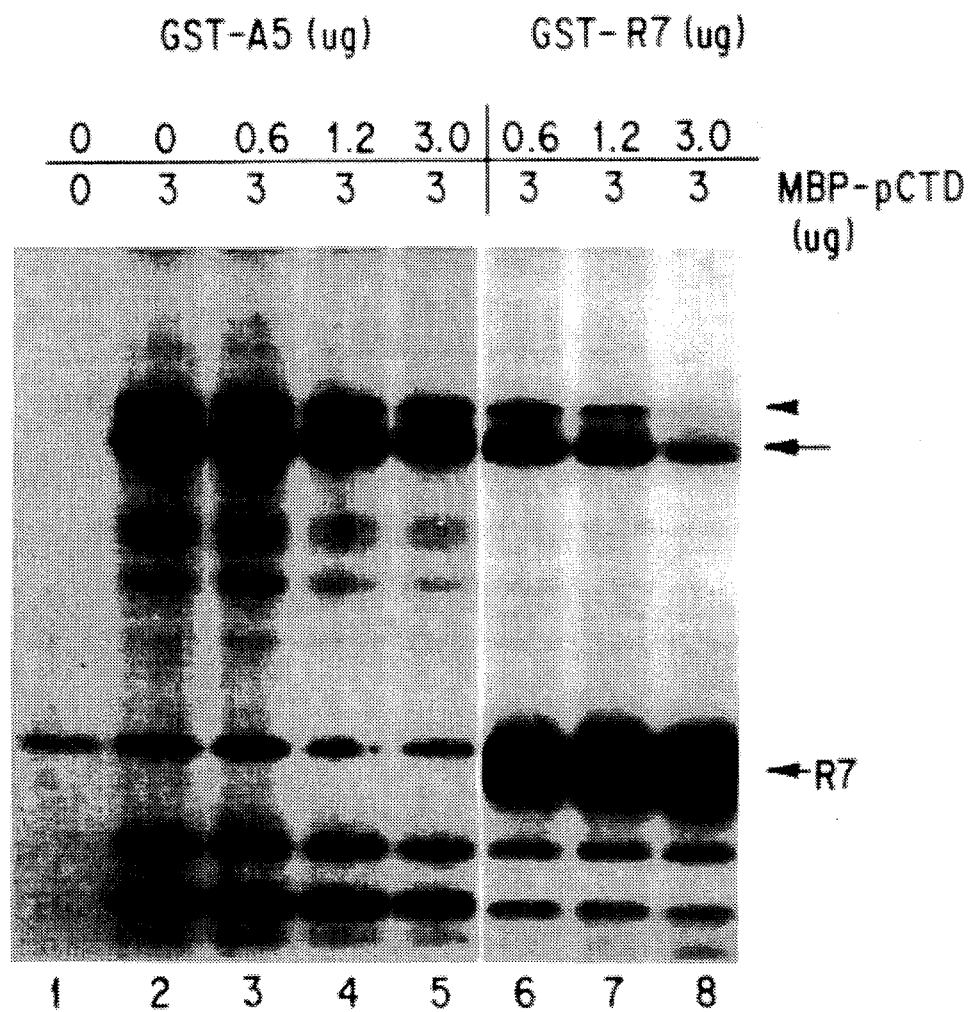
FIG. 4 is an autoradiogram comparing phosphorylation of MBT-pCTD by Plasmodium nuclear extract in the absence and presence of either GST-A5 substrate analog or GST-R7 substrate analog.

Results for the GST-$A5_{13}$ analog and the GST-$R7_{13}$ analog are shown in FIG. 4 (where lanes 1–5 contained varying amounts of GST-A5 and lanes 6–8 contained varying amounts of GST-R7; lane 1 contained no fusion protein substrate and lanes 2–8 contained MBP-pCTD). The Plasmodium nuclear extract phosphorylated and mobility-shifted the MBP-pCTD fusion protein substrate as expected (FIG. 4, lane 2; arrow=unshifted, arrowhead=shifted). Little effect on substrate phosphorylation was seen when an increasing amount of the GST-$A5_{13}$ analog was added to a set of reactions with a constant amount of substrate (FIG. 4, lanes 3–5). In contrast, adding increasing amounts of the GST-$R7_{13}$ analog reduced the amount of mobility-shifted product (FIG. 4, lanes 6–8, arrowhead); at an equiweight ratio of GST-$R7_{13}$ analog-to-substrate there was significant inhibition of the Plasmodium CTD kinase activity responsible for generating the shifted band (FIG. 4, lane 8).

In other experiments it was found that the GST-$R7_{13}$ analog did not similarly inhibit the corresponding human CTD kinase activity (data not shown).

Additional analogs listed in Table 1 (GST-$A2_{13}$ and GST-$A2A5_{13}$) were similarly tested. The GST-$A2A5_{13}$ analog displayed inhibitory activity at very high concentrations; a ratio of approximately 10:1 analog-to-substrate was required before inhibition was noted. These results indicated that changing $Lys_7$ to $Arg_7$ altered the affinity for the enzyme such that the analog functioned as a competitive inhibitor of the Plasmodium, but not the human, CTD kinase.

Further, these experiments indicated that it is the Ser at position 5 that is phosphorylated, since the GST-$A5_{13}$ analog was not labeled (FIG. 4, lanes 3–5) whereas the GST-$R7_{13}$ analog was labeled (FIG. 4, the major band in lanes 6,7 & 8 marked R7). Thus the R7 analog acted as an inhibitor but was also a substrate, as it contains serine residues and is phosphorylated. A2A5 is slightly inhibitory. Replacing lysine (L7) with arginine (R7) was found to increase the peptide affinity for the enzyme, while replacing the serine at the fifth position with alanine (A5) prevented phosphorylation.

These data indicate that substrate analog GST-$R7_{13}$ inhibits the Plasmodium CTD kinase but not the human CTD kinase.

EXAMPLE 7

Additional Plasmodium CTD Kinase Inhibitor

The analog A5R7 is prepared for use as a Plasmodium CTD kinase inhibitor. $Lys_7$ is substituted for $Arg_7$ to increase the peptide affinity for the enzyme, as was noted with the use of $GST-R7_{13}$ analog (Example 6). The results of Example 6 also indicated that the Ser at position 5 is phosphorylated, and therefore alanine is substituted for $Ser_5$ to prevent phosphorylation. The resulting A5R7 peptide (Tyr-Ser-Pro-Thr-Ala-Pro-Arg; SEQ ID NO:7) acts as an inhibitory peptide for Plasmodium CTD kinase, and is not phosphorylated.

EXAMPLE 8

Synthetic Peptide Inhibitors of Plasmodium CTD Kinase

As noted above, a fusion protein containing repeats of the Plasmodium CTD sequence Tyr-Ser-Pro-Thr-Ser-Pro-Lys (SEQ ID NO:2) is a substrate for the Plasmodium enzyme. Synthetic peptide variants of this inhibitor will also function as inhibitors, in parallel with the above results for fusion proteins. In view of studies on inhibitors of other protein kinases (see e.g., Knighton et al., *Science* 253, 414–420 (1991) and references therein), it may be necessary to prepare and screen an extensive set of sequence variants and test the variants for inhibitory activity, using techniques known in the art.

A set of variant peptides are synthesized in accordance with techniques known in the art, such as chemical synthesis, or through recombinant DNA procedures, as discussed above. Peptides are then characterized as to inhibition of Plasmodium CTD kinase using, for example, assays as described above. Results of these tests guide the design of the next set of peptides. Repeats of this iterative process lead to the design of effective inhibitors.

EXAMPLE 9

Peptide Mimetics as Inhibitors of Plasmodium CTD Kinase

Non-peptide mimetics are synthesized based on the knowledge of effective peptide inhibitors of protozoan CTD kinase. The results and information generated during the process of identifying peptide inhibitors is used to guide the synthesis of peptide mimetics. Non-protein drug design may be carried out using computer graphic modeling. The crystal structure of the CTD kinase is modeled using data from x-ray crystallography studies of other protein kinases or nuclear magnetic resonance (NMR) imaging. Two protein kinases whose crystal structures are known are the catalytic subunit of cAMP-dependent protein kinase (see Knighton et al, *Science*, 253, 407 (1991) and the cyclin-dependent kinase 2 (CDK2) (see De Bondt et al., *Nature*, 363, 595 (1993). Modeling of protein kinase structure based on the known structure of other kinases by homology is discussed in Knighton et al., *Science*, 258, 130 (1992) and Marcote et al., *Mol. Cell. Biol.*, 13, 5122 (1993). The structures of related proteins are used as a template in computer modeling of CTK1. An inhibitor able to attach to the active sites of the model is then developed and assayed as above.

The foregoing is illustrative of the present invention and is not to be construed as limiting thereof. The invention is defined by the following claims, with equivalents of the claims to be included therein.

---

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

Tyr  Ser  Pro  Thr  Ser  Pro  Ser
    1                        5

( 2 ) INFORMATION FOR SEQ ID NO:2:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide (xi) SEQUENCE DESCRIPTION: SEQ ID NO:2:

Tyr Ser Pro Thr Ser Pro Lys
1               5

(2) INFORMATION FOR SEQ ID NO:3:

(i) SEQUENCE CHARACTERISTICS:
 (A) LENGTH: 7 amino acids
 (B) TYPE: amino acid
 (C) STRANDEDNESS: single
 (D) TOPOLOGY: linear (ii) MOLECULE TYPE: peptide (xi) SEQUENCE DESCRIPTION: SEQ ID NO:3:

Tyr Ala Pro Thr Ser Pro Lys
1               5

(2) INFORMATION FOR SEQ ID NO:4:

(i) SEQUENCE CHARACTERISTICS:
 (A) LENGTH: 7 amino acids
 (B) TYPE: amino acid
 (C) STRANDEDNESS: single
 (D) TOPOLOGY: linear (ii) MOLECULE TYPE: peptide (xi) SEQUENCE DESCRIPTION: SEQ ID NO:4:

Tyr Ser Pro Thr Ala Pro Lys
1               5

(2) INFORMATION FOR SEQ ID NO:5:

(i) SEQUENCE CHARACTERISTICS:
 (A) LENGTH: 7 amino acids
 (B) TYPE: amino acid
 (C) STRANDEDNESS: single
 (D) TOPOLOGY: linear (ii) MOLECULE TYPE: peptide (xi) SEQUENCE DESCRIPTION: SEQ ID NO:5:

Tyr Ala Pro Thr Ala Pro Lys
1               5

(2) INFORMATION FOR SEQ ID NO:6:

(i) SEQUENCE CHARACTERISTICS:
 (A) LENGTH: 7 amino acids
 (B) TYPE: amino acid
 (C) STRANDEDNESS: single
 (D) TOPOLOGY: linear (ii) MOLECULE TYPE: peptide (xi) SEQUENCE DESCRIPTION: SEQ ID NO:6:

Tyr Ser Pro Thr Ser Pro Arg
1               5

That which is claimed is:

1. A method of detecting blood-borne Plasmodium in a mammalian subject, comprising the steps of:

(1) collecting a sample containing red blood cells from a mammalian subject;

(2) treating said sample to lyse red blood cells and any Plasmodium present in said sample;

(3) contacting said sample with (a) a Plasmodium C-terminal domain (CTD) kinase substrate and (b) a phosphorus donor;

(4) detecting hyperphosphorylation of said substrate; and (5) correlating the presence of hyperphosphorylation with the presence of blood-borne Plasmodium in said mammalian subject.

2. The method of claim 1, wherein said phosphorus donor is selected from the group consisting of adenosine triphosphate (ATP), uridine triphosphate (UTP), guanosine triphosphate (GTP), cytidine triphosphate (CTP), adenosine diphosphate (ADP), uridine diphosphate (UDP), guanosine diphosphate (GDP), and cytidine diphosphate (CDP).

3. The method of claim 1, wherein said phosphorus donor comprises radiolabelled phosphorus.

4. The method of claim 1 wherein said blood-borne Plasmodium is selected from the group consisting of *Plasmodium falciparum, Plasmodium vivax, Plasmodium malariae, Plasmodium ovale*, and *Plasmodium berghei*.

5. The method of claim 1 wherein said Plasmodium C-terminal domain (CTE) kinase substrate is selected from the group consisting of:

a peptide of amino acid sequence (Tyr-Ser-Pro-Thr-Ser-Pro-Lys)$_n$ (SEQ ID NO:2);

a peptide of amino acid sequence (Tyr-Ala-Pro-Thr-Ala-Pro-Lys)$_n$ (SEQ ID NO:5); and a peptide of amino acid sequence (Tyr-Ser-Pro-Thr-Ser-Pro-Arg)$_n$ (SEQ ID NO:6);

where n is from one to one hundred.

* * * * *

UNITED STATES PATENT AND TRADEMARK OFFICE
CERTIFICATE OF CORRECTION

PATENT NO. : 5,565,327                                    Page 1 of 2
DATED      : October 15, 1996
INVENTOR(S) : Greenleaf et al.

It is certified that error appears in the above-identified patent and that said Letters Patent is hereby corrected as shown below:

Col. 1, line 12, after "II" insert --in--;

Col. 2, line 57, replace "Ser-pro" with --Ser-Pro--;

Col. 4, line 66, replace "Liet al." with --Li et al.--;

Col. 24, line 2, replace "CTE" with --CTD--;

Col. 19, Sequence Listing, General Information, Number of Sequences, replace "6" with --7--;

Col. 21:  insert sequence ID No:7 as follows

--(2)    INFORMATION FOR SEQ ID NO:7:

(i)  SEQUENCE CHARACTERISTICS:
        (A)  LENGTH:  7 amino acids
        (B)  TYPE:  amino acid
        (C)  STRANDEDNESS:  single
        (D)  TOPOLOGY:  linear

UNITED STATES PATENT AND TRADEMARK OFFICE
CERTIFICATE OF CORRECTION

PATENT NO. : 5,565,327  
DATED : October 15, 1996  
INVENTOR(S) : Greenleaf, et al Page 2 of 2

It is certified that error appears in the above-indentified patent and that said Letters Patent is hereby corrected as shown below:

(ii) MOLECULE TYPE: peptide (xi) SEQUENCE DESCRIPTION: SEQ ID NO:7:

Tyr Ser Pro Thr Ala Pro Arg
1            5--;

Signed and Sealed this

Twenty-second Day of July, 1997

Attest:

BRUCE LEHMAN

Attesting Officer

Commissioner of Patents and Trademarks